US006477394B2

(12) United States Patent
Rice et al.

(10) Patent No.: US 6,477,394 B2
(45) Date of Patent: *Nov. 5, 2002

(54) NON-INVASIVE MEASUREMENT OF BLOOD COMPONENTS USING RETINAL IMAGING

(75) Inventors: Mark J. Rice, Johnson City, TN (US); Robert H. Sweat, Jr., Lexington, KY (US); James M. Rioux, Lexington, KY (US); William T. Williams, Jonesborough, TN (US); Wilson Routt, Lexington, KY (US)

(73) Assignee: Fovioptics, Inc., Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/952,491

(22) Filed: Sep. 12, 2001

(65) Prior Publication Data

US 2002/0072658 A1 Jun. 13, 2002

Related U.S. Application Data

(63) Continuation of application No. 09/534,782, filed on Mar. 24, 2000, now Pat. No. 6,305,804.
(60) Provisional application No. 60/165,195, filed on Nov. 12, 1999, and provisional application No. 60/126,212, filed on Mar. 25, 1999.

(51) Int. Cl.[7] ................................. A61B 5/00
(52) U.S. Cl. ....................................... 600/318
(58) Field of Search ................................ 351/200, 221; 600/318, 319, 315, 316, 320, 323, 328; 424/9.6; 356/40, 41

(56) References Cited

U.S. PATENT DOCUMENTS 6,305,804 B1    10/2001   Rice et al.

Primary Examiner—George Manuel
(74) Attorney, Agent, or Firm—Foley & Lardner

(57) ABSTRACT

Illuminating light of selected wavelengths in the visible or infrared range is projected through the pupil of the eye onto the fundus, and the light reflected back and out through the pupil is detected and analyzed, preferably using the area of the optic disk for analyzing the retinal vessels overlying the optic disk. Specific wavelengths of illuminating light may be chosen for each blood component to be analyzed depending on the spectral characteristics of the substance being analyzed. The reflected image from the retina may be used to measure non-photoreactive blood components such as hemoglobin, and photoreactive components such as bilirubin. For the measurement of photoreactive components, images may be taken before and after, or during, illumination of the eye with light at wavelengths which will affect the photoreactive analyte, enabling measurements of the concentration of the analyte.

37 Claims, 7 Drawing Sheets

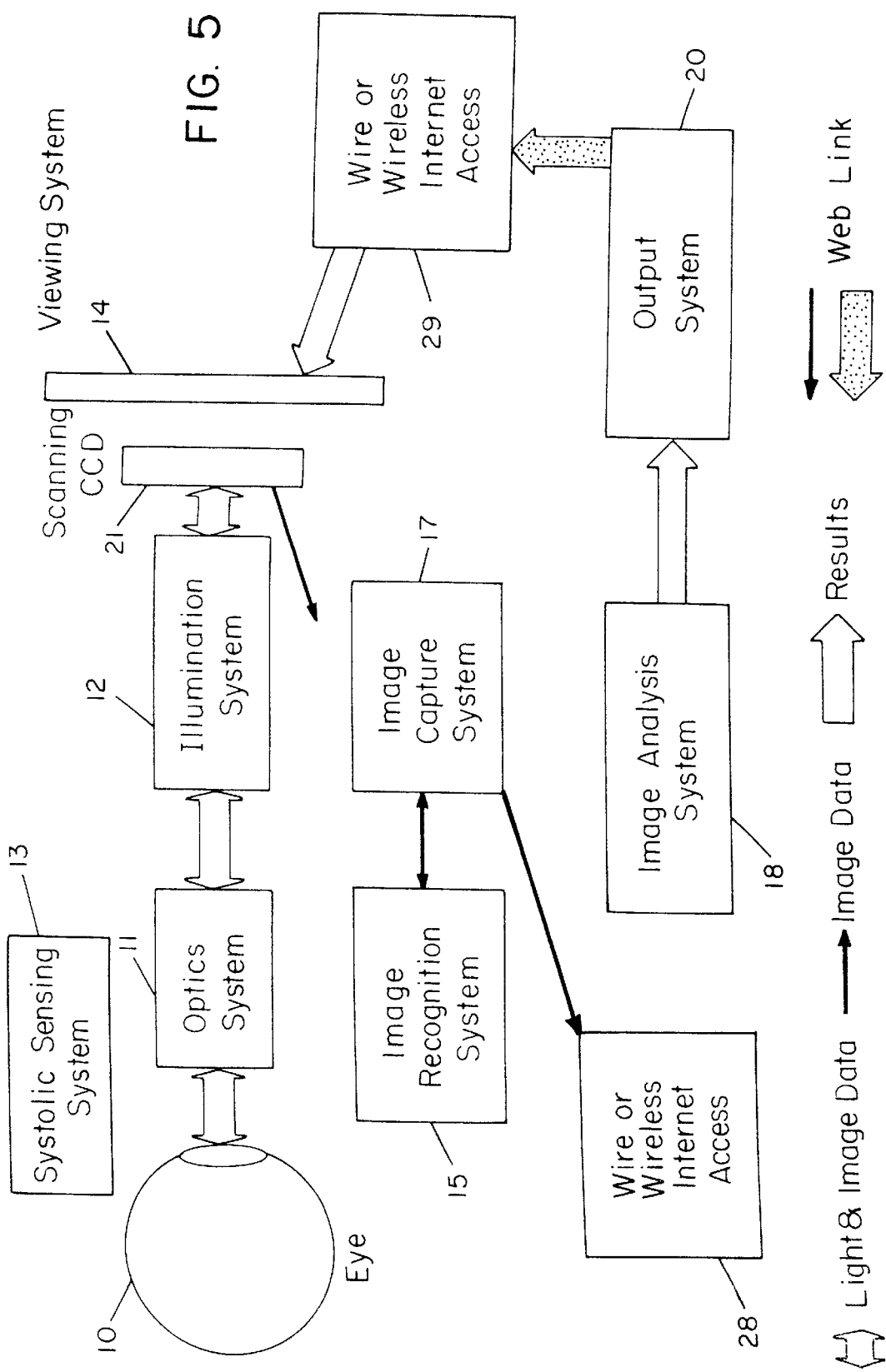

NON-INVASIVE MEASUREMENT OF BLOOD COMPONENTS USING RETINAL IMAGING

This application is a continuation of application Ser. No. 09/534,782, filed Mar. 24, 2000, now U.S. Pat. No. 6,305,804, which claims the benefit of provisional patent application No. 60/165,195, filed Nov. 12, 1999, and of provisional patent application No. 60/126,212, filed Mar. 25, 1999.

FIELD OF THE INVENTION

This invention pertains to the field of non-invasive in vivo measurement of blood components such as glucose, hemoglobin, and bilirubin.

BACKGROUND OF THE INVENTION

The measurement of the concentration of blood components such as hemoglobin and glucose has required the drawing of a blood sample for in vitro analysis. The need to draw blood for analysis is undesirable for several reasons, including discomfort to the patient, the time required of medical personnel to draw and handle the samples, and the potential risk of spread of disease through punctures of the skin. Repeated drawing of blood samples is especially undesirable in infants. Many diabetics must test their blood up to six times a day to monitor their blood glucose levels. It would thus be desirable to be able to obtain fast and reliable estimates of the concentration of blood components in blood, such as hemoglobin and glucose, through a simple and non-invasive technique. Prior efforts have involved an examination of blood in the skin or extremities, such as fingers and ear lobes, or in observable surface blood vessels, but these efforts have had limited practical success due to the presence of tissue components that interfere with accurate reading of only the concentration of blood components.

There are approximately four million newborns in the United States alone each year. About 50% of newborns are clinically jaundiced from elevated bilirubin levels. If the serum bilirubin reaches very high levels during the post-natal period, kernicterus, neural damage resulting from sustained high levels of serum bilirubin, may occur. Frequent monitoring of serum bilirubin is critical to the care of these infants. Of the newborns that have recognizable jaundice during the first 5 days of life, 1.7 million receive at least one blood test for bilirubin. Of those tested, about 700,000 undergo phototherapy treatment; these infants receive an estimated two to three additional blood tests. Presently, blood is drawn through the heel of the neonate, resulting in occasional infections and other complications. Other drawbacks to this process are its high cost and the delay in lab results reaching the physician. Recently introduced non-invasive devices for measuring bilirubin do not provide the accuracy level required to diagnose or treat elevated serum bilirubin levels, rendering them virtually useless in practice.

SUMMARY OF THE INVENTION

The present invention combines the accuracy of in vitro laboratory testing of blood components and the advantages of rapidly-repeatable non-invasive technology. The invention utilizes a hand-held or stationary instrument for retinal imaging that allows non-invasive measurement of certain blood components in the retinal blood vessels. Illuminating light of selected wavelengths in the visible or infrared range is projected into the eye onto the fundus, and the light reflected back and out (e.g., through the pupil) is detected and analyzed, preferably using the area of the optic disk for analyzing the retinal vessels overlaying the optic disk for most blood components to be measured. Specific wavelengths of illuminating light may be chosen for each blood component to be analyzed depending on the spectral characteristics of the particular substance being analyzed. The reflected image from the retina is utilized to measure blood components, such as hemoglobin, glucose and bilirubin.

The utilization of the retina as a site for obtaining blood component data has several advantages, including the ease of visualizing the data because of the natural window provided by the eye. The reflected light from the fundus at visually significant wavelengths is much less scattered than light reflected from the skin or mucous membranes since the eye is naturally immune to scatter. The retina creates a uniform background for imaging, and the optical devices and techniques required for obtaining retinal images have been extensively developed and studied because of the need for ophthalmologists to image the retina for diagnosis of disease states. In addition, the blood flow to the retina is very even and repeatable even across a number of disease states. For example, although patients in shock have reduced blood flow to the skin and mucous membranes, allowing false data to be obtained with current technology that examines the skin and mucous membranes, the body maintains even blood flow to the retina except in states of extremely low blood pressure. Furthermore, in the present invention, there is no physical contact required between the device and the skin or mucous membranes, thereby eliminating the potential for transmission of infectious agents associated with devices that require patient contact. The device may be rested upon the orbit of the patient for ease of use and, if desired, a disposable plastic cover may be used to further minimize the risk of transmission of infectious agents. Such a cover may be transparent and fully cover the device, or not, depending upon requirements of the imaging system and the need to prevent incidental contact with the device.

In accordance with the invention, a hand-held or stationary instrument for retinal imaging may be used to obtain non-invasive measurement of photoreactive analytes, an example of which is serum bilirubin. Illuminating light of selected wavelengths in the visible range is projected into the eye onto the fundus. Specific wavelengths of illuminating light are chosen so that serum bilirubin can be measured. Analysis of the reflected image from the fundus is utilized to measure bilirubin. Although measurement of the reflected light from the vessels overlying the optic disk is preferred, in accordance with the invention, it is also typically possible to obtain bilirubin measurements from light reflected from the fundus generally.

During disease states when the serum bilirubin levels are above normal (e.g., newborn jaundice), bilirubin is extruded from the choroid into the nerve layer of the retina. During newborn jaundice, this nerve layer stains yellow from the elevated bilirubin levels. This yellow color is directly proportional to the elevated serum bilirubin levels and changes rapidly with changes in serum bilirubin. The bilirubin molecule exhibits peak absorption of light at 470 nm. However, when exposed to light at or near this wavelength, the molecule breaks down into optically inactive molecules. The intact bilirubin molecule reflects light at and near a wavelength of approximately 550 nm (yellow light), and is not affected by this light. In the present invention, the retina of the patient's eye may first be imaged with light that does not break down bilirubin, e.g., light at a wavelength of 550 nm with little or no light at 470 nm. The intensity of the reflected light at or near the maximum reflection wavelength of 550 nm is detected. Then the retina is imaged again using light that breaks down bilirubin, e.g., using light at 470 nm followed by or combined with light at 550 nm, which is projected into the eye. The reflected light at 550 nm that is passed out through the pupil is detected to image the retina a second time. With the addition of light at 470 nm, the bilirubin molecule is rendered optically inactive and will no longer reflect at 550 nm. The difference in the reflected image intensity at 550 nm from the first image to the second image is a function of the bilirubin concentration. A neural network or other processing technique may be used to analyze the two data sets of the images captured by the retinal camera.

Further objects, features and advantages will be apparent from the following detailed description when taken in conjunction with the accompanying drawings.

BRIEF DESCRIPTION OF THE DRAWINGS

In the drawings:

FIG. 5 is a schematic diagram of a further apparatus in accordance with the invention that incorporates a communications link to a remote processing system.

DETAILED DESCRIPTION OF THE INVENTION

The present invention may be used to measure various analytes. These analytes may be photoreactive or non-photoreactive. Table 1 below summarizes examples of the preferred methodologies in accordance with the invention for the measurement of photoreactive and non-photoreactive analytes. However, it is understood that these are only illustrative of the analytes that may be measured using the present invention.

TABLE 1

| | Methodologies | | |
|---|---|---|---|
| Target Molecule: | Non-Photoreactive Analyte | | Photoreactive Analyte |
| Examples: | Hemoglobin | Glucose | Bilirubin |
| Illumination: | Visible Light | IR illumination | Discrete wavelength visible light |
| | IR illumination | | |
| Target Site: | Retinal disk vasculature | Retinal disk vasculature | Retina |
| Imaging: | Single image | Multiple images | Multiple time lapsed images at different wavelengths |
| | | Scanned sensor array | |

Device Description

Figure 1:
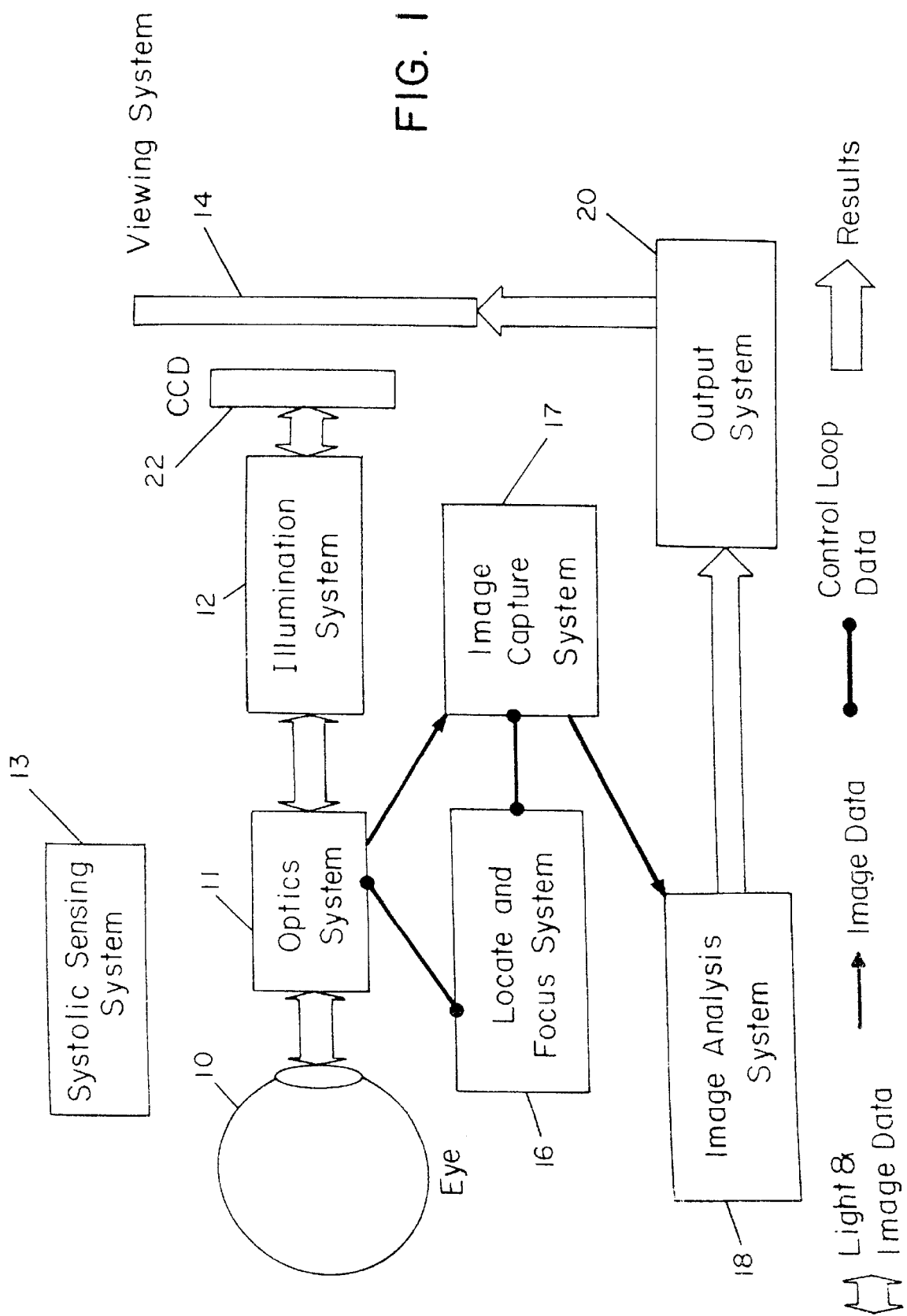
FIG. 1 is a schematic diagram of an apparatus for measurement of the concentration of blood components in accordance with the invention.

With reference to the drawings, FIG. 1 illustrates a blood analysis apparatus of the invention in conjunction with the eye of the patient, shown illustratively at 10 in FIG. 1. The blood analysis apparatus includes an optics system 11 comprised of lenses for projecting illuminating light onto the fundus, generally although not necessarily directly through the pupil, and for receiving the light reflected from the fundus passed out through the pupil, and for focusing that light to form an image. The lenses preferably include a final lens which can be positioned close to (e.g., approximately 3 mm from) the cornea of the eye, providing a 10 to 30 degree conical view of the retina to be illuminated and imaged. Such lens systems are of conventional design and are utilized for macroview lens systems in retinal video cameras.

An illumination system 12 provides selected illuminating light for viewing and imaging the retina. The illumination system is preferably a monochromatic or multiple discrete wavelength light source that provides light for viewing and imaging the retina. Preferably, the system provides light for viewing and imaging coaxially to reduce the likelihood of extraneous reflections from the interior or exterior of the eye. The light from the illumination system may be projected through the pupil. The frequency content of this light source is selected dependent upon the compound to be analyzed. Illumination light may be composed of two (or more) separate lighting systems, such as a xenon strobe, or multiple laser diodes, for imaging, and a halogen source for viewing. Infrared imaging may be done utilizing a filtered halogen or laser diode source. The light is reflected from the fundus of the eye 10 and passed through the pupil opening of the eye to the optics system 11 and through the illumination system 12, entering, e.g., a charge coupled device (CCD) detector 22. The illumination system 12 may be similar to systems used in existing non-mydriatic fundus cameras, preferably modified to provide a coaxial design for illumination and imaging. A viewing system 14, for example, a liquid crystal display (LCD) screen, may receive the image data and display the image for use by the operator for initially locating the patient's retina, based on an image from the optical system in real time. A coaxial "scene" or visual target may be included in the visual field of the device so that a patient can fixate his or her eye on this scene and reduce eye motion. In addition to reducing eye motion, the location of this visual target will bring the optic disk into the approximate center of the CCD detector. In devices intended for children, the scene may include a visually pleasant object such as a familiar animal. In the currently commercially available video cameras designed for retinal imaging, the LCD (or other display) screen is typically located on a desktop power source that is attached to the hand-held camera by a cable. While such displays may be used in the present invention, the LCD screen (or other display device) is preferably placed on the back of the hand-held camera unit, so that the operator can more easily locate the retina, having the patient's eye and the LCD screen in the same line-of-sight. Current retinal video camera systems that may be modified and utilized in the invention and which include an optics system 11 and an illumination system include the Nidek NM100 Hand-Held Non-Mydriatic Fundus Camera and the Topcon TRC-50EX (TRC-NW5S/TRC-NW5SF) Non-Mydriatic Retinal Camera. The Nidek NM100 camera utilizes a coaxial imaging system with an infrared source, with imaging done through reflected light outside the optical system. Although the invention may be carried out with a dilated eye pupil, it is preferable that the imaging of the retina be carried out without requiring dilation of the pupil for speed of measurement and patient convenience. The camera preferably includes a shield (not shown) to prevent ambient light from entering the optical system 11 to minimize extraneous reflections and the introduction of optical noise.

The optical system 11 also interfaces with a locate and focus system 16, which utilizes feedback from an image capture system 17, also interfaced to the optic system 11, to automatically find and bring the optic disk into focus. A convolver or other pattern recognition software may be utilized to locate the optic disk area by finding the circular pattern of the optic nerve area. After using the pattern recognition information to more precisely locate the optic nerve area in the center of the viewing field, the image may then be magnified using a series of lenses in the optics system 11 such that the optic disk area virtually fills the active area of the CCD (or other detector). The optical system preferably tracks the movement of the fundus while zooming the optics such that the optic disk is centered and occupies most of the optical field of view. The optical system may be formed to track the motion of the fundus through a motor drive system that slightly gimbals the lens system. This motion system is driven and controlled in a closed loop manner utilizing the feedback of the pattern recognition software.

The image capture system 17 is selectively controlled by the operator and uses feature and pattern recognition to drive the locate and auto focus system 16 to capture and store an appropriate image for analysis. Image capture itself is analogous to the function provided by a "digital still camera." The image capture system may utilize feature and pattern recognition to drive the locate and focus system to capture and store an appropriate image for analysis. Commercially available pattern recognition software may be used. Actual imaging is preferably timed based on the patient's blood flow, which is preferably sensed from blood vessels through the patient's skin around the ocular structure through a systolic sensing system 13. The light reflected from the retina is preferably detected and an image formed at the time of systole, thus ensuring the maximum blood flow in the vasculature of the retina. Detection of the patient's systolic state can be made through any commonly known means such as commercially available blood pressure transducers. An image analysis system 18 is interfaced with the image capture system 17 to analyze the light reflected from the retina to quantitatively determine the amount of the particular target analyte compound present. The results may be displayed to the operator via the output system 20. This system presents results as well as any feedback associated with the acquisition of the data, and may include an LCD display screen or other display devices.

Figure 2:
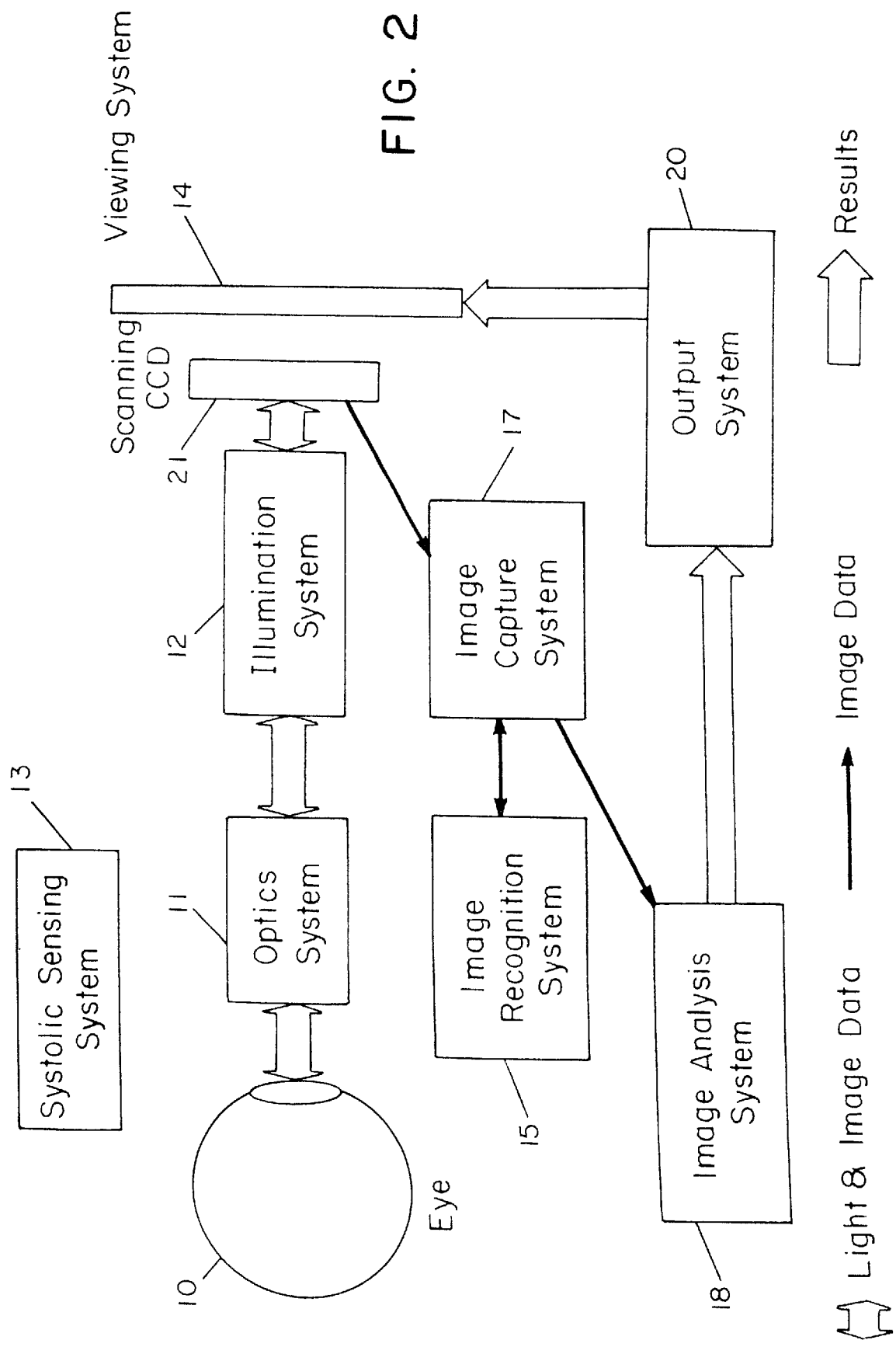
FIG. 2 is a schematic diagram of a modified form of the apparatus for measurement of blood components in accordance with the invention.

A modified imaging methodology as shown in FIG. 2 may also be used wherein an imaging device 21 functions in a scanning mode (which may be similar to that utilized in common video cameras) to provide multiple images of the retina to the image capture system 17. The image recognition system 15 then acts to select a valid image from the series of images stored by the image capture system 17. Once selection of an appropriate image is made, calculation of the magnitude of the desired analyte proceeds using the image analysis system 18 as before. Image validity is based on focus, closeness to center of the fundus, and obliqueness of the fundus in the image.

Figure 3:
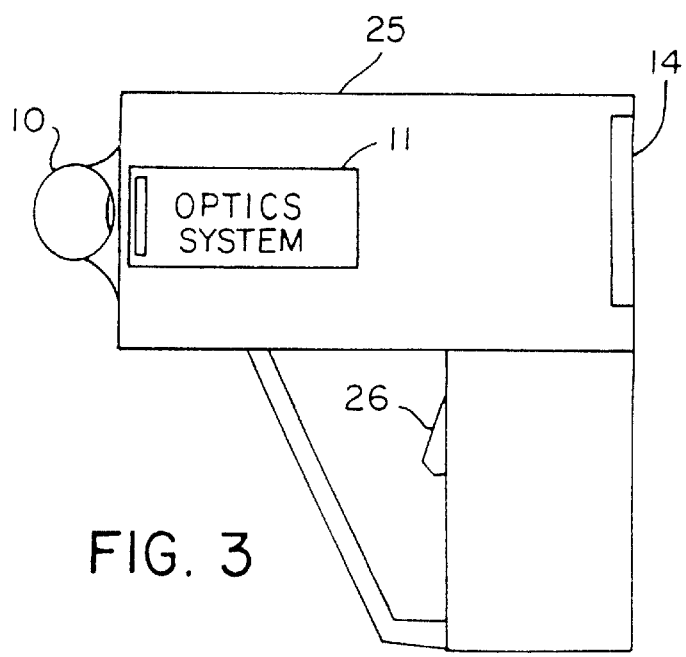
FIG. 3 is a schematic side view of a hand-held illumination and camera system that may be utilized in accordance with the invention.
Figure 4:
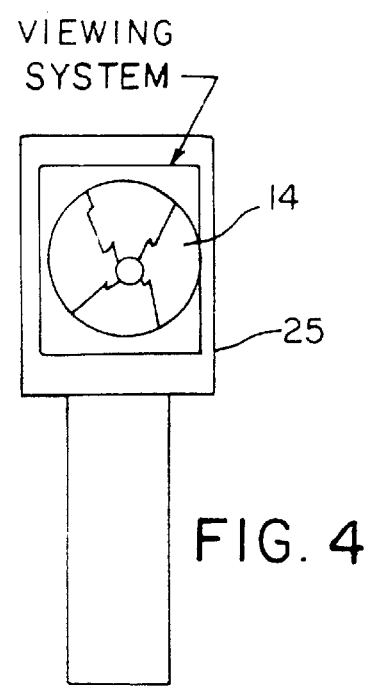
FIG. 4 is an illustrative front view of the illumination and camera system of FIG. 3.

FIG. 3 illustrates a hand-held camera and illumination unit 25 for the analysis system of the invention in which the optic system 11 is mounted, and FIG. 4 illustrates the output viewing system 14 at the back end of the hand-held unit 25 to enable the operator to review the image being obtained of the retina on a real-time basis. If desired, a disposable transparent plastic (e.g. polyethylene, polystyrene, polypropylene, etc.), which is selected to transmit light in the wavelengths required, may be used to cover the unit 25 during use and then disposed of to minimize the risk of transmission of infection. Eye infections are particularly common in newborns and a cover would assist in the prevention of these infections. Furthermore, the cover may include a soft portion (e.g. foam) that comes into contact with the skin around the orbit. This makes the cover comfortable and, in addition, prevents ambient light from entering into the camera lens during measurements.

Currently available CCD detectors may not be sensitive to wavelengths longer than approximately 1000 nm. In measuring analytes requiring the sensing of these longer wavelengths, an alternative approach may be used. The illumination source may instead scan across the area of interest on the retina, with the reflected beam being read by a single sensor (or a small multiplicity of sensors) that are sensitive in the infrared (IR) wavelengths above normal CCD sensitivity. This method may be used to digitally reconstruct the retinal image if desired.

As illustrated in FIG. 5, image processing and analysis may take place at a location remote from the clinical setting by using a wired or wireless internet link (or dedicated communication link) to transfer data from the image capture system 17 to a central computer at a remote location (i.e., anywhere in the world linked by the internet) at which the image analysis system 18 is implemented. The output data from the output system 20 may be transferred back through an access link 29 to the viewing system 14 at the clinic (or to another location, as desired).

Non-Photoreactive Analyte (Hemoglobin) Measurement

In one implementation of the device for the detection of hemoglobin using multiple beam splitters, the image of the optic disk returning from the eye may be split into three simultaneous and equal images. Each image is then passed through a filter with the preferred wavelengths for the images of 640, 766 and 800 nm. Different wavelengths of light are used for the analysis of other substances such as glucose. Although these preferred wavelengths will yield accurate measurement of hemoglobin, other wavelengths in the visible or near IR may also be used effectively by this invention for hemoglobin.

Figure 11:
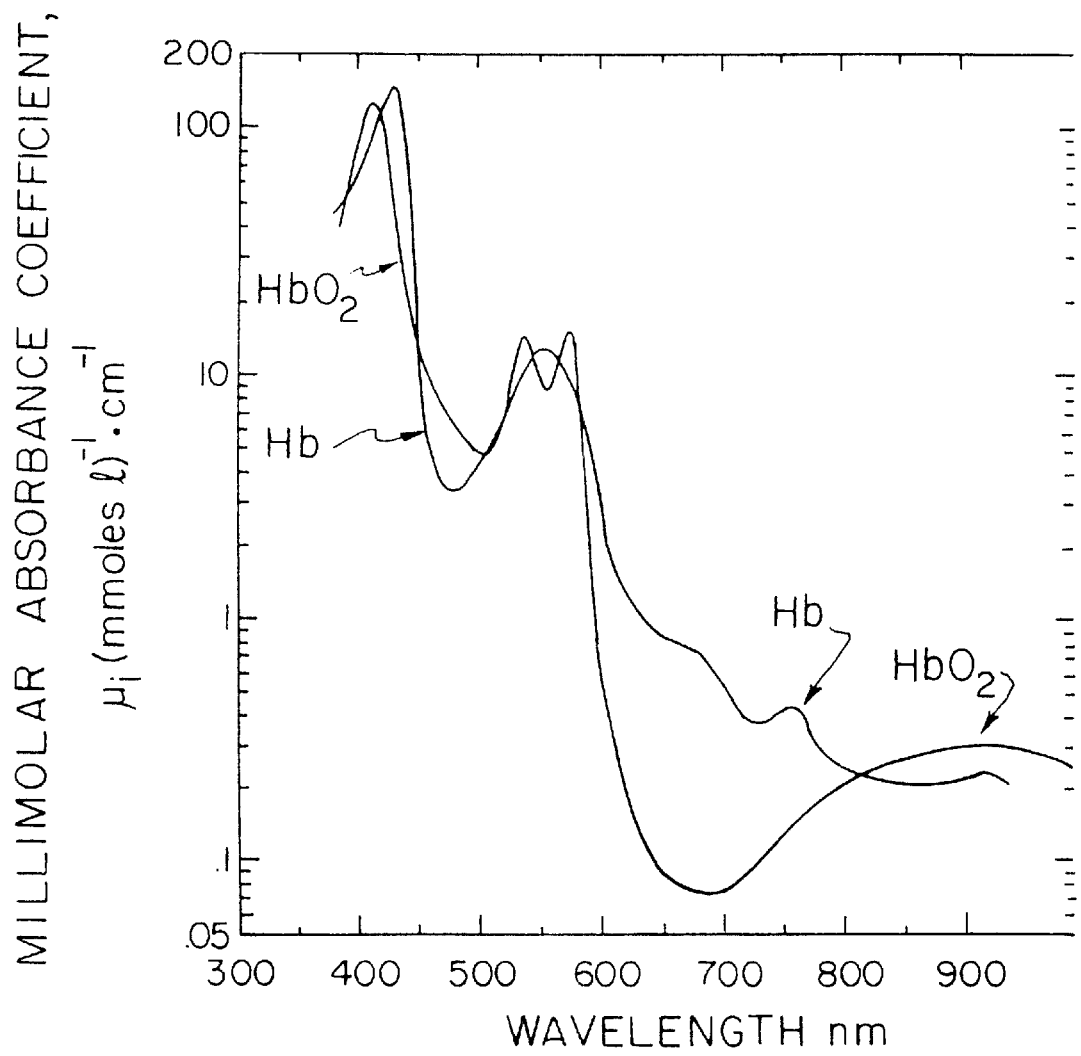
FIG. 11 are graphs of light absorption as a function of wavelength for deoxyhemoglobin and oxyhemoglobin.

To obtain accurate measurements of hemoglobin concentration without having to account for different levels of oxygen saturation, the measurement of hemoglobin may be carried out in the present invention using wavelengths of light at which the extinction coefficients for oxyhemoglobin and deoxyhemoglobin match. Thus, the total absorption of energy at that wavelength will be proportional to the total hemoglobin. Examples of such wavelengths are 550 nm and 800 nm. Absorption curves for oxyhemoglobin ($HbO_2$) and deoxyhemoglobin (Hb) as a function of illumination wavelength are shown in FIG. 11. As illustrated therein, the absorption curves are closely matched in the wavelength range from about 380 nm to 580 nm, and particularly from about 530 nm to 580 nm, allowing most (or all) wavelengths in these ranges to be used.

The areas that are preferably used for analysis are the retinal arteries and veins overlaying the optic disk. Previous work by Hickam et al. suggested that when the optic disk is illuminated with light directed toward the fundus, the optic disk acts as a light source directing the light back through the retinal vessels that lay over the disk. See, John B. Hickam, et al., "A Study of Retinal Venous Blood Oxygen Saturation in Human Subjects by Photographic Means," Circulation, Vol. XXVII, March, 1963, pp. 375–385. Hickam, et al. believed that these vessels then functioned as cuvettes, filled with blood, that could be analyzed by the spectral pattern that is measured from the light passing through these vessels and emitted out through the pupil. In actuality, light does not pass through these vessels and reflect off the optic disk and then pass through these vessels again as suggested in Hickam, et al. Instead, light reflects directly off the surfaces of these vessels and the blood components within these vessels. In the present invention, the retinal arteries are the sub-target areas that are analyzed by measuring the amplitude of the signal at each selected wavelength. This is done by determining the effective reflected image intensity of the pixels for the sub-target areas corresponding to the arteries at each selected wavelength. Within the sub-target area, the peak concentration of blood is determined by viewing the peak absorption at each measured wavelength. The sub-target area is then normalized by this peak and then may be averaged using any common digital averaging technique, such as a convolver. Within the sub-target area, a histogram is created to represent different signal levels after averaging. These data comprised of histogram values and values representing the rate of change in local intensity are then the direct input into an analysis program, e.g., a neural network, for analysis. A computer implemented neural network is preferably utilized to analyze the pixel data for comparison to known blood concentrations. A preferred type of neural network is Back Propagation.

The effect of differences in illumination from one retinal image to another is preferably neutralized by comparing the background illumination of the optic disk to the vessel illumination and "zeroing" for differences in illumination. This allows the input from the sub-target areas to be consistent from patient to patient and camera to camera.

Although the present invention is well suited to be carried out on a "real time" basis with the apparatus of FIGS. 1 and 2 as described above, it may be implemented using photographic fundus images which are scanned and processed. As an example of the present invention using photographic images, a group of individuals was tested to measure hemoglobin levels utilizing the present invention. A standard in vitro test was also performed on a sample of blood drawn from each individual. The clinical data were obtained as follows. Each ophthalmologist in the clinic agreed to refer for study patients that already had their eyes dilated. A physician asked the patient if they would agree to have their eyes photographed and to allow blood to be obtained for a hemoglobin test. An informed consent document was signed by each patient. A retinal photographer with the clinic took all of the retinal photographs. The slide film used was Kodachrome 64 Select, 24 exposures per roll. The photographer took photos of each eye, with the fovea centered in the picture. The exact same conditions were used for each photograph including aperture, shutter speed, and illumination. A code was given for each patient to insure confidentiality and to allow accurate tracking of each patient. The code appeared on each photograph and the same code appeared on the blood tube.

A licensed phlebotomist obtained antecubital blood samples from each patient. These samples were drawn with vacutainers into purple-top tubes for later analysis. The tubes were stored cold and run the same evening. Following the analysis, the blood tubes were saved if later analysis were required. The blood samples were analyzed for hemoglobin content with a HemoCue® B-Hemoglobin Analyzer. The machine was calibrated with calibration slides. This device is CLIA certified and the technician who analyzed the samples was also CLIA certified. Each sample was run three times on the machine to ensure accurate results. These results were recorded along with the patient's ID code. Kodachrome 64 Select Slide Film was used for each retinal photograph. The film was sent to Kodak for processing. The Kodak development lab used the same lot of chemicals for all of the slides. The developed slides were then scanned into a digital format (jpeg files) with a Polaroid Sprintscan 4000 scanner.

Multiple images of each subject were taken, and images were selected for analysis based on uniformity of illumination, quality of focus, obliqueness of fovea to illumination axis, and systole status. The (normalized) green portion of the RGB image data in the jpeg file was used for analysis, where green $=G/(R+G+B)$. As illustrated in FIG. 11, in the green wavelength range (about 500 nm to 550 nm), the absorption of oxy- and deoxyhemoglobin is similar. The image analysis proceeded with the following steps for each selected image:

Find the optic disk.

Create a circular area of data entirely within the optic disk that is less in diameter than the optic disk. Convolve the data in this circle with a small convolver (0.5 mm) to smooth the data.

Find the maximum and minimum levels of green in pixels within the circle. Use this min. level to normalize the values of all pixels within the circle.

Compute the gradient of green within the circle.

Find the centroid of the gradient magnitude.

Construct a circle (subtarget) of the image that is approximately 0.5 mm in diameter centered at the centroid and within the disk. (This procedure locates a sub-target area within a retinal vessel in the optic disk.)

Using the data in the pixels having green magnitudes in the range of 25–45% of the maximum level of green in the subtarget, create a histogram of this area with 5 buckets for values and 5 buckets for derivative magnitudes. For each magnitude range, calculate the average derivative (gradient) magnitude and average magnitude.

These values then become the input for a learning algorithm, such as a neural network simulation, which is trained to associate measured hemoglobin with the data sets.

The neural net employed for exemplification was the "Back Propagation" neural net which is contained in the MATLAB Toolbox of MATLAB Version 5.3.

The neural net is trained with the data sets determined above by the following technique:

(a) remove one data set (representing one image) from the total number of sets.

(b) use the data sets remaining to train the neural net mentioned above.

(c) use the trained neural net to calculate a hemoglobin value from the data set left out at step (a) above.

By repeating the neural net calculation above, a curve was constructed of non-invasively calculated values versus actual lab values.

Figure 10:
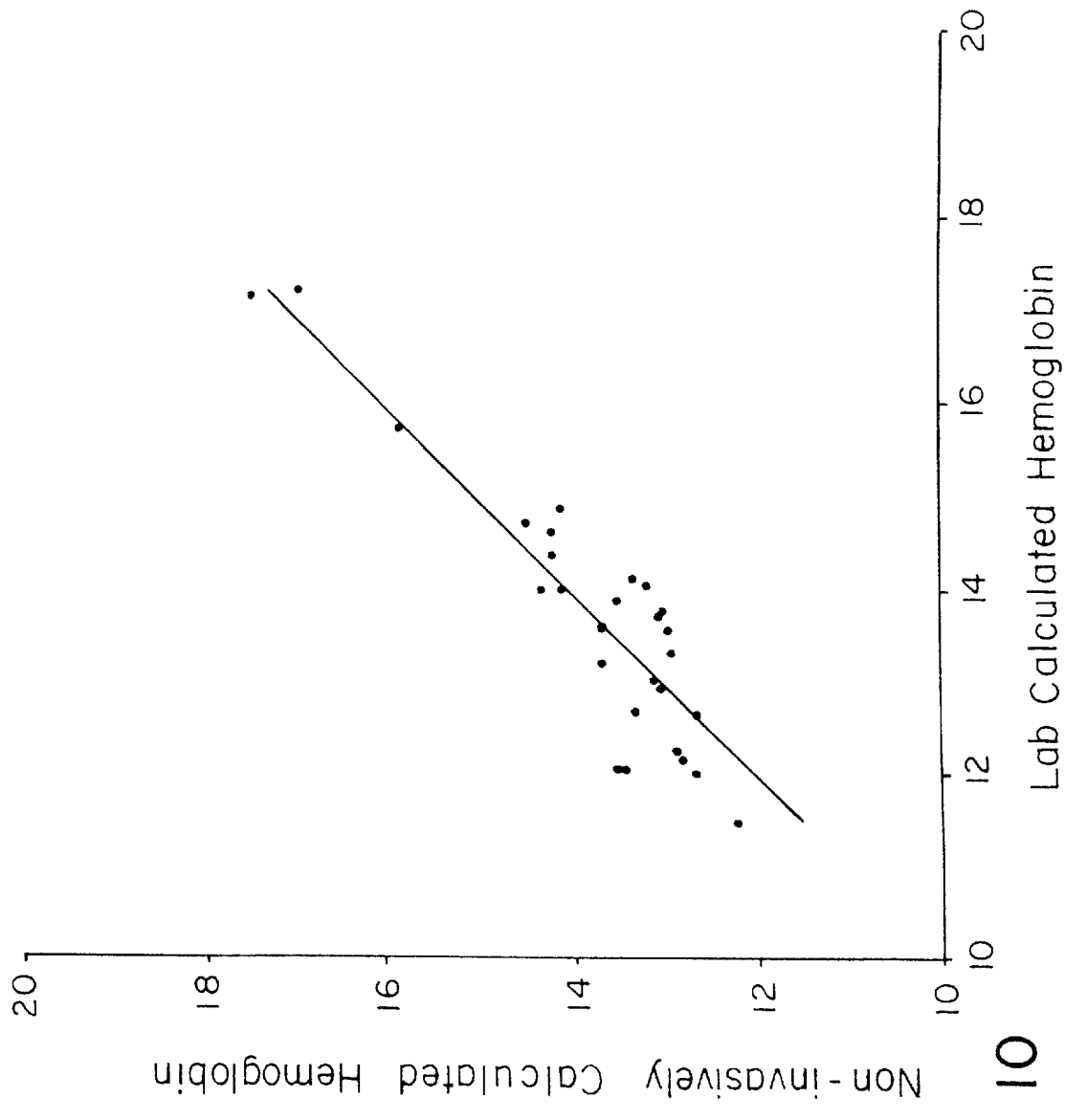
FIG. 10 is a graph illustrating the correlation between hemoglobin concentration measured in accordance with the invention versus concentration measured by a standard in vitro technique.

Correlation data showing the measurements of hemoglobin concentration for each individual as determined in accordance with the present invention versus the hemoglobin measurement values obtained by the in vitro laboratory measurements are shown in FIG. 10. These data indicate a strong correlation, 0.89, between the measurements obtained by the present invention and measurements obtained by standard in vitro laboratory techniques.

The results of the analysis of the serum concentration values of the blood components may be displayed on an output system 20 to the operator. The output system 20 may utilize the LCD screen 14 of the viewing system to present data to the operator as well as feedback on any problems occurring with the acquisition of the image or the device. In the event that the image is not acceptable and will not allow the device to calculate accurate blood values, the output system 20 preferably prompts the operator to capture another image.

In a subset of the patient population, because of particular anatomical characteristics of the eye, various degrees of light scattering may be encountered. This scattering of the light may be the result of various disease states including senile cataracts. A polarized light source may be included in the device to measure the degree of scattering. The returned light at orthogonal polarization may be used as a measure of scattering. This data is fed into the neural network as the scattering variable from patient to patient to allow the device to account for this variable.

Several analytes that are measured with the device of the invention are also secreted into the anterior chamber of the eye. The aforementioned embodiment of the device directs light through the anterior chamber to the retina. The image returned from the retina again passes through this area of the eye. The presence of the analyte in this section of the eye could create false data sets and render the device inaccurate. Therefore, when measuring analytes such as glucose that are present in the anterior chamber, the light may be directed along an alternate path to the retina. The illuminating light emitting from the device may be directed toward the retina at an angle into the eye just lateral to the cornea near the corneoscleral junction (limbus). This angle avoids light passing through the anterior chamber of the eye. The exiting light would then be detected at an angle at the opposite side of the eye, again just lateral to the cornea near the corneoscleral junction (limbus). Although this area near the surface of the eye is not optically clear in the visual range of the electromagnetic spectrum, it is transparent in the longer wavelengths (>1000 nm) needed to measure analytes such as glucose.

Photoreactive Analyte (Bilirubin) Measurement

Further in accordance with the present invention, the concentration of a photoreactive analyte may be determined by taking advantage of its photoreactivity. For example, bilirubin concentration may be determined by taking advantage of the fact that the bilirubin molecule exhibits peak absorption of light at 470 nm, and that at or near this wavelength the molecule breaks down into optically inactive molecules. The bilirubin molecule will also effectively break down when exposed to light in the range of 470 nm±30 nm. The bilirubin molecule ordinarily reflects light maximally at or near a wavelength of approximately 550 nm (yellow light). In accordance with the invention, a time lapse image of the retina may be made wherein the first image is illuminated at 550 nm (±30 nm) followed by a second image illuminated at 470 nm (±30 nm) and a third image illuminated at 550 nm (±30 nm). The second and third images are separated in time sufficiently that the photoreactive analyte will change chemical state. In the case of bilirubin, the change is a almost instantaneous and the two wavelengths may be projected simultaneously as well as sequentially. The first exposure provides an image including the photoreactive analyte (bilirubin in this example) while the third exposure provides a reference point for this patient without the photoreactive analyte (bilirubin in this example) present. The concentration of the photoreactive analyte can be computed using a neural net or other well known analysis process based on differences in the first and third exposures. Light at wavelengths other than 550 nm may also be used to illuminate the retina as long as such wavelengths do not precipitate a photo-chemical reaction from the analyte (bilirubin in this example).

Figure 9:
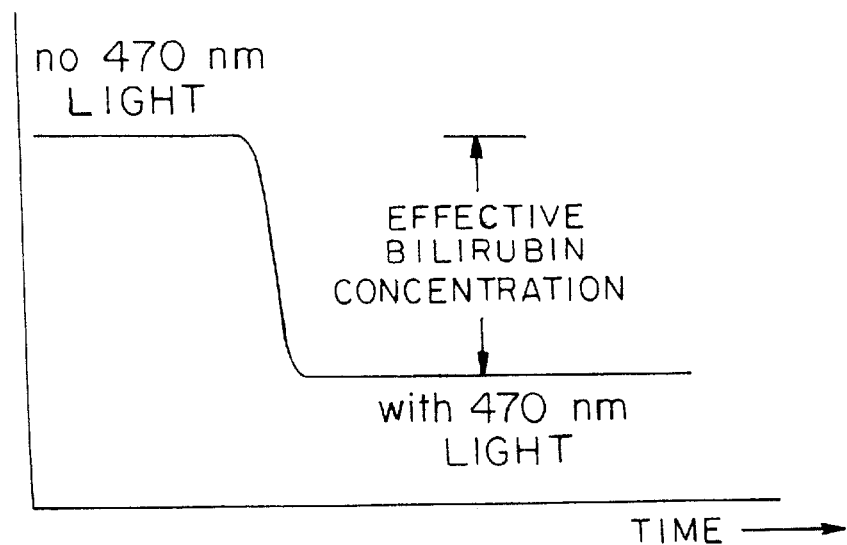
FIG. 9 is a graph of the intensity of light at 550 nm reflected from the retina showing the effect of single pulse illumination at 470 nm.
Figure 6:
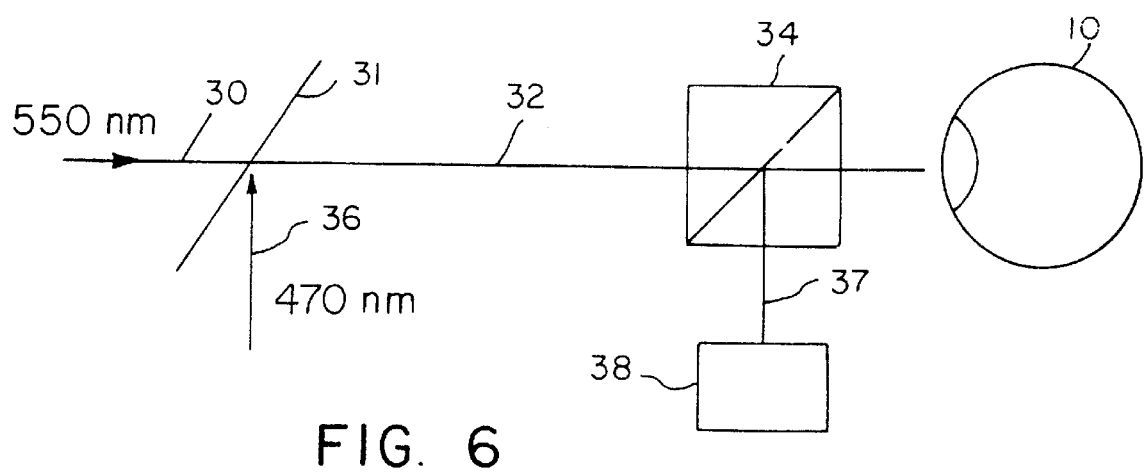
FIG. 6 is a simplified schematic diagram of apparatus in accordance with the invention for measuring bilirubin concentration in blood.
Figure 7:
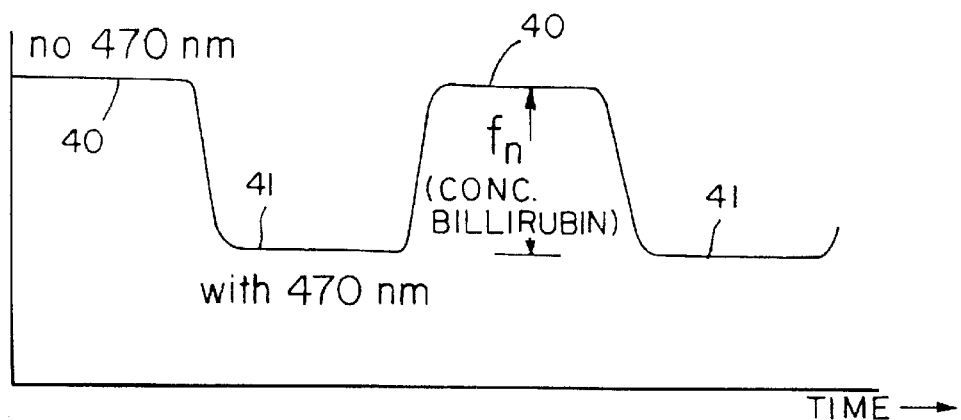
FIG. 7 is an illustrative graph of intensity of light at 550 nm reflected from the retina as a function of time, showing the effect of the periodic illumination of the eye at 470 nm.
Figure 8:
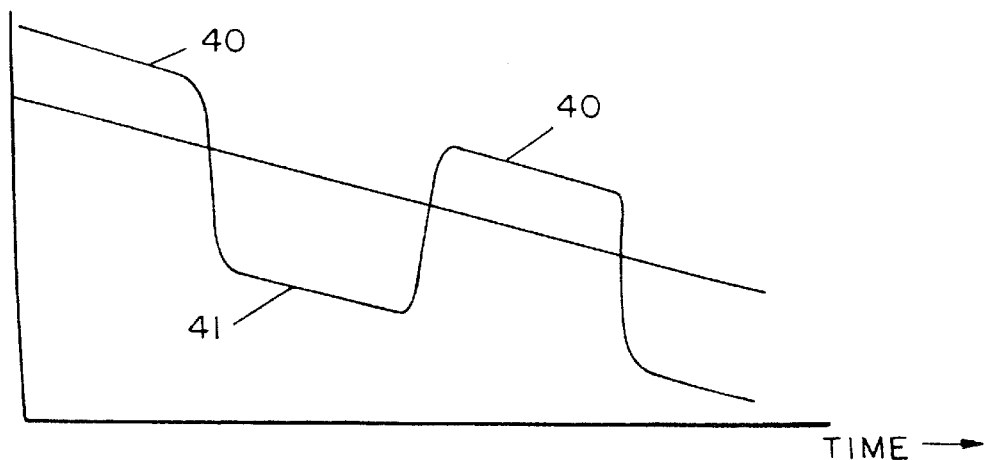
FIG. 8 is an illustrative graph, similar to FIG. 7, of reflected light intensity over time showing the effect of changes in blood flow in the retinal vessels.

In one embodiment of the invention, with reference to FIG. 6 and with bilirubin as the target analyte, light at a wavelength of 550 nm is directed on a beam 30 to a partially transmissive and reflective mirror 31, passing therethrough on a beam path 32 to a beam splitter 34 and thence to the eye 10. The light at a wavelength of 550 nm is directed at the retina to create a first image. Light from a source at 470 nm is provided on a path 36 to the partial mirror 31 and is reflected on the path 32 through the beam splitter 34 to the eye 10. The reflected light at 470 nm is directed by the element 34 on a path 37 to an absorber 38. The light at 470 nm is pulsed onto the retina at very short time intervals. With each pulsation of light at 470 nm, the bilirubin molecule is rendered optically inactive and is not reflected from the retina at 550 nm. As illustrated in FIG. 7, the reflected 550 nm light intensity is high at the intervals 40 when there is no 470 nm light illumination and is lower at the intervals 41 at which the 470 nm light is applied. The difference in reflected light intensity from the peak to the trough with each pulsation is a function of the bilirubin concentration. The time intervals 40 and 41 chosen will be dependent on the blood flow to the retina. FIG. 8 illustrates the change over time with blood flow. A time interval is required such that there is a partial filling up of the retinal circulation by blood that contains bilirubin. The invention may also be implemented using a single pulse application of 470 nm light to measure the bilirubin concentration as shown in FIG. 9.

The data corresponding to the returned light at 550 nm comprised of pixel values are then the direct input into a neural network or other well known procedure for analysis.

A neural network is preferably utilized to analyze the pixel data for comparison to known blood concentrations of bilirubin. The difference in pixel data from reflected light at 550 nm before and after the 470 nm light pulse is a direct function of the serum bilirubin level.

The results of the serum values of the bilirubin may be displayed on an output system 20 to the operator. The output system 20 may utilize the LCD screen of the viewing system to present data to the operator as well as feedback on any problems occurring with the acquisition of the image or the device. In the event that the image is not acceptable and will not allow the device to calculate accurate bilirubin values, the output system 20 preferably prompts the operator to capture another image. Other photo-reactive analytes may be measured in a manner analogous to the measurement of bilirubin as discussed above.

It is understood that the invention is not limited to the embodiments set forth herein as illustrative, but embraces all such forms thereof as come within the scope of the following claims.

What is claimed is:

1. Apparatus for detection of the concentration of a blood component in an individual comprising:
    (a) means for projecting light having selected wavelengths into an eye of an individual to illuminate the fundus;
    (b) means for detecting the light reflected from the fundus and for forming an image of a portion of the fundus containing blood vessels; and
    (c) means for analyzing selected wavelength components in the detected light from the blood vessels in the image to determine the concentration of a selected blood component.

2. The apparatus of claim 1 wherein the selected blood component is hemoglobin.

3. The apparatus of claim 1 wherein the selected blood component is glucose.

4. The apparatus of claim 1 wherein the selected blood component is bilirubin.

5. The apparatus of claim 1 wherein the means for analyzing selected wavelength components analyzes only light from the regions of the image corresponding to blood vessels.

6. The apparatus of claim 1 wherein the light projected into the eye by the means for projecting contains wavelengths in the visible or near infrared range and wherein the means for detecting the light reflected from the fundus includes means for detecting the light in the visible or near infrared range.

7. The apparatus of claim 1 wherein the means for forming an image forms an image of the blood vessels in the region overlying the optic disk of the eye and wherein the means for analyzing the wavelength components analyzes the light reflected from the optic disk.

8. The apparatus of claim 1 including means for sensing the blood flow of the individual being tested to detect systole and for using this information to time the detecting of the light reflected from the fundus and forming of an image.

9. The apparatus of claim 1 wherein the means for detecting the light and forming an image forms multiple images of the fundus at discrete times over a period of time and selects an image from the multiple images and analyzes that image to determine the concentration of the blood component.

10. The apparatus of claim 1 wherein the means for detecting the light and forming an image splits the detected light into multiple images that are passed through filters that pass different wavelengths to provide multiple filtered images, and the means for analyzing analyzes the multiple filtered images to determine the concentration of the blood component.

11. The apparatus of claim 10 wherein the blood component is hemoglobin and the multiple images are filtered to pass light centered at wavelengths of 640 nm, 766 nm and 800 nm.

12. The apparatus of claim 1 including means for transmitting data corresponding to the image over a communications link to a remote location, and wherein the means for analyzing selected wavelength components is located at the remote location.

13. The apparatus of claim 1 wherein the means for projecting light into the eye projects light through the pupil of the eye onto the fundus.

14. The apparatus of claim 1 wherein the means for projecting light into the eye projects light on a path at an angle into the eye just lateral to the cornea, near the corneoscleral junction.

15. Apparatus for detecting the concentration of a photoreactive analyte in the blood of an individual comprising:
    (a) means for projecting light into the eye of an individual to illuminate the fundus that contains wavelengths not including light at wavelengths that will break down the photoreactive analyte and for detecting the light reflected from the fundus to determine the intensity of the reflected light at these wavelengths;
    (b) means for projecting light into the eye to illuminate the fundus containing wavelengths that break down the photoreactive analyte and for projecting light into the eye to illuminate the fundus containing the wavelengths that do not break down the photoreactive analyte, and for detecting the intensity of such light reflected from the fundus; and
    (c) means for determining the difference between the intensity of light detected with no wavelengths that break down the photoreactive analyte projected on the fundus and the intensity of light detected when light which breaks down the photoreactive analyte has been projected onto the fundus, from which the analyte concentration may be determined.

16. The apparatus of claim 15 wherein the target analyte is bilirubin or an associated molecule.

17. The apparatus of claim 16 wherein the means for projecting light that does not break down bilirubin projects light that does not contain wavelengths in the range of 470 nm±30 nm.

18. The apparatus of claim 17 wherein the light projected that does not break down bilirubin contains light centered at 550 nm.

19. The apparatus of claim 17 wherein the means for projecting light that breaks down bilirubin projects light having wavelengths in the range of 470 nm±30 nm.

20. The apparatus of claim 16 wherein the means for projecting light into the eye containing wavelengths that break down the photoreactive analyte and for projecting light containing the wavelengths that do not break down the photoreactive analyte projects light containing wavelengths centered at 470 nm and at 550 nm simultaneously.

21. The apparatus of claim 16 wherein the means for projecting light into the eye containing wavelengths that break down the photoreactive analyte and for projecting light containing the wavelengths that do not break down the photoreactive analyte projects light centered at 470 nm followed thereafter by projecting light containing wavelengths centered at 550 nm to illuminate the fundus, and wherein the light centered at 550 nm reflected from the fundus is detected.

22. A method of detecting the concentration of a photoreactive analyte in the blood of an individual comprising:
   (a) projecting light into the eye of the individual to illuminate the fundus that contains wavelengths not including light at wavelengths that will break down the photoreactive analyte and detecting the light reflected from the fundus and for forming an image of a portion of the fundus containing blood vessels and determining the intensity of the reflected light at these wavelengths in the image;
   (b) projecting light into the eye to illuminate the fundus containing wavelengths that break down the photoreactive analyte, and projecting light into the eye to illuminate the fundus containing the wavelengths that do not break down the photoreactive analyte and detecting the light reflected from the fundus and forming an image of a portion of the fundus containing blood vessels and determining the intensity of the reflected light in the image at the wavelengths that do not break down the photoreactive analyte; and
   (c) determining the difference between the intensity of light detected with no wavelengths that break down the photoreactive analyte projected on the fundus and the intensity of light detected when light which breaks down the photoreactive analyte has been projected onto the fundus, from which the analyte concentration may be determined.

23. The method of claim 22 wherein the target analyte is bilirubin or an associated molecule.

24. The method of claim 23 wherein in the steps of projecting light that do not break down bilirubin, the light projected does not contain wavelengths in the range of 470 nm±30 nm.

25. The method of claim 24 wherein the light projected that does not break down bilirubin contains light centered at 550 nm.

26. The method of claim 24 wherein the step of projecting light that breaks down bilirubin comprises projecting light having wavelengths in the range of 470 nm±30 nm.

27. The method of claim 23 wherein step (b) includes projecting light containing wavelengths centered at 470 nm and at 550 nm simultaneously.

28. The method of claim 23 wherein step (b) is carried out by projecting light centered at 470 nm followed thereafter by projecting light containing wavelengths centered at 550 nm to illuminate the fundus, and wherein the light centered at 550 nm reflected from the fundus is detected.

29. The method of claim 22 wherein in the steps of determining the intensity of the reflected light in the image, the intensity of reflected light is determined only from the regions of the image corresponding to blood vessels.

30. Apparatus for detecting the concentration of a photoreactive analyte in the blood of an individual comprising:
   (a) means for projecting light into the eye of an individual to illuminate the fundus that contains wavelengths not including light at wavelengths that will break down the photoreactive analyte and means for detecting the light reflected from the fundus and for forming an image of a portion of the fundus containing blood vessels and determining the intensity of the reflected light at these wavelengths in the image at the wavelengths that do not break down the photoreactive analyte;
   (b) means for projecting light into the eye to illuminate the fundus containing wavelengths that break down the photoreactive analyte and for projecting light into the eye to illuminate the fundus containing the wavelengths that do not break down the photoreactive analyte, and means for detecting the light reflected from the fundus and for forming an image of a portion of the fundus containing blood vessels and for determining the intensity of the light reflected from the fundus; and
   (c) means for determining the difference between the intensity of light detected with no wavelengths that break down the photoreactive analyte projected on the fundus and the intensity of light detected when light which breaks down the photoreactive analyte has been projected onto the fundus, from which the analyte concentration may be determined.

31. The apparatus of claim 30 wherein the target analyte is bilirubin or an associated molecule.

32. The apparatus of claim 31 wherein the means for projecting light that does not break down bilirubin projects light that does not contain wavelengths in the range of 470 nm±30 nm.

33. The apparatus of claim 32 wherein the light projected that does not break down bilirubin contains light centered at 550 nm.

34. The apparatus of claim 31 wherein the means for projecting light that breaks down bilirubin projects light having wavelengths in the range of 470 nm±30 nm.

35. The apparatus of claim 31 wherein the means for projecting light into the eye containing wavelengths that break down the photoreactive analyte and for projecting light containing the wavelengths that do not break down the photoreactive analyte projects light containing wavelengths centered at 470 nm and at 550 nm simultaneously.

36. The apparatus of claim 31 wherein the means for projecting light into the eye containing wavelengths that break down the photoreactive analyte and for projecting light containing the wavelengths that do not break down the photoreactive analyte projects light centered at 470 nm followed thereafter by projecting light containing wavelengths centered at 550 nm to illuminate the fundus, and wherein the light centered at 550 nm reflected from the fundus is detected and the intensity of such light is determined.

37. The apparatus of claim 31 wherein in the means for determining the intensity of the reflected light in the image, the intensity of reflected light in the image is determined only from the regions of the image corresponding to blood vessels.

* * * * *